United States Patent [19]

Stone

[11] Patent Number: 5,293,875
[45] Date of Patent: Mar. 15, 1994

[54] IN-VIVO MEASUREMENT OF END-TIDAL CARBON MONOXIDE CONCENTRATION APPARATUS AND METHODS

[75] Inventor: Robert T. Stone, Sunnyvale, Calif.

[73] Assignee: Natus Medical Incorporated, San Carlos, Calif.

[21] Appl. No.: 899,261

[22] Filed: Jun. 16, 1992

[51] Int. Cl.$^5$ ............................................... A61B 5/00
[52] U.S. Cl. .............................. 128/719; 128/204.22; 128/205.23
[58] Field of Search ................... 128/716, 719, 204.22, 128/204.23, 205.22

[56] References Cited

U.S. PATENT DOCUMENTS

| | | | |
|---|---|---|---|
| 3,977,394 | 8/1976 | Jones et al. | 128/2.07 |
| 4,423,739 | 1/1984 | Passaro et al. | 128/719 |
| 4,831,024 | 5/1989 | Vreman et al. | 514/185 |
| 4,968,887 | 11/1990 | Wong | 250/343 |
| 5,003,985 | 4/1991 | White et al. | 364/413.08 |

OTHER PUBLICATIONS

Yeung et al. "Automatic End Expiratory Air Sampling Device for Breath Hydrogen Test in Infants, The Lancet", vol. 337, pp. 90-93 (Jan. 1991 Product Literature—Z-World Engineering Little Giant Minature Microcontroller (One page).
Product Literature—Servomex Mode 1505 $Co_2$ Infra-red Transducer borchure (2 pages) and technical note (9 pages).
Product literature—KNF Diaphragm Micro Pump Type NMP 02 (2 pages).

*Primary Examiner*—Lee S. Cohen
*Assistant Examiner*—Robert L. Nasser
*Attorney, Agent, or Firm*—David Hoxie Faithfull & Hapgood

[57] ABSTRACT

A noninvasive device and methods for measuring the end-tidal carbon monoxide concentration in a patient's breath, particularly newborn and premature infants. The patient's breath is monitored. An average carbon monoxide concentration is determined based on an average of discrete samples in a given time period. The ratio of the end-tidal portion of the breath flow sample is separately determined, preferably based on monitoring the level of carbon dioxide in the gas sample and identifying the carbon dioxide concentration levels corresponding to the end-tidal portion of the breath sample. The sensed carbon monoxide level is converted to the end-tidal carbon monoxide level by subtracting the ambient carbon monoxide level and dividing the remainder by the ratio of end-tidal breath to breath in the breath sample. An easy to use microcontroller-based device containing a carbon dioxide detector, a carbon monoxide detect and a pump for use in a hospital, home, physician's office or clinic by persons not requiring high skill and training is described.

50 Claims, 10 Drawing Sheets

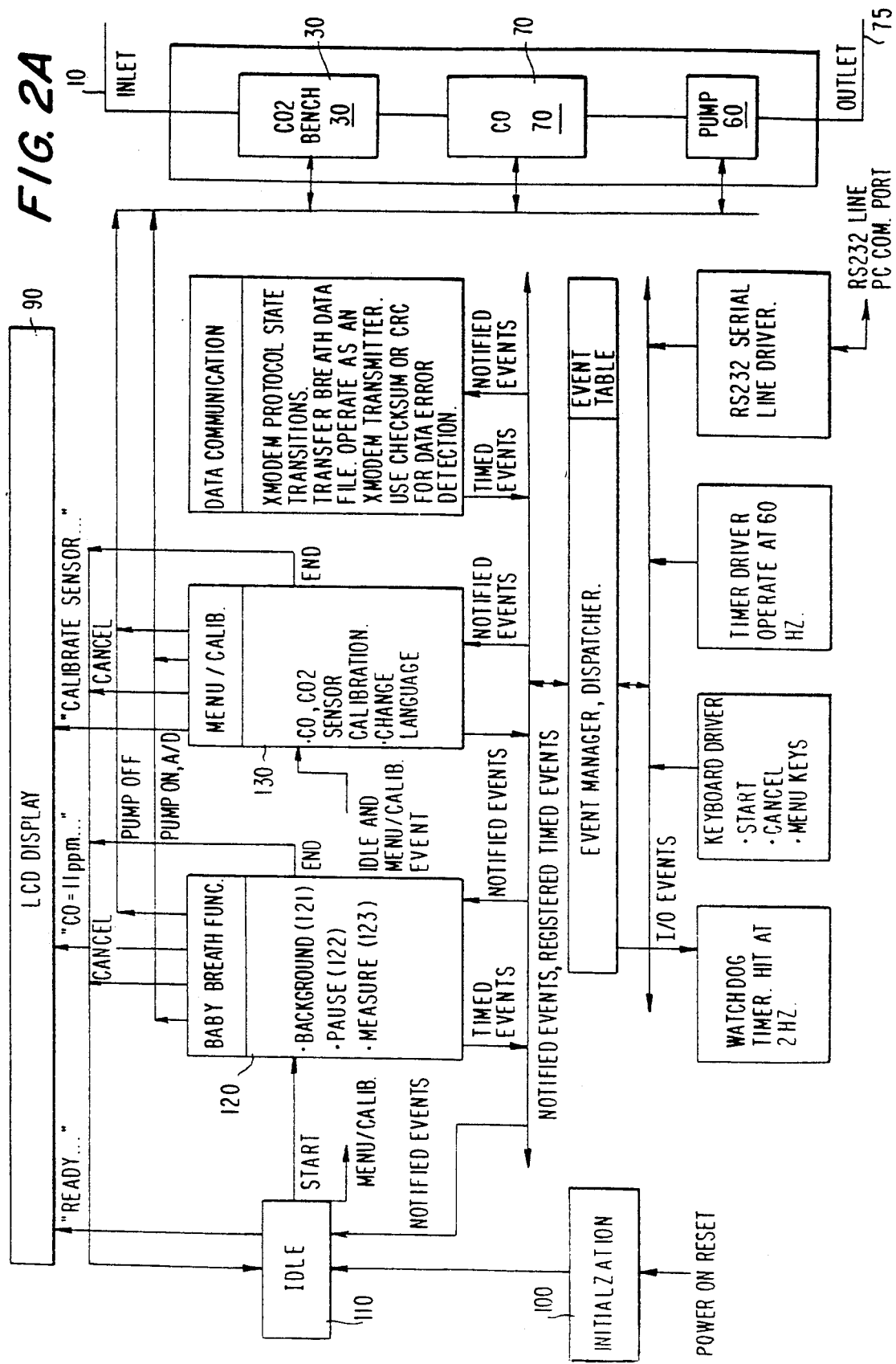

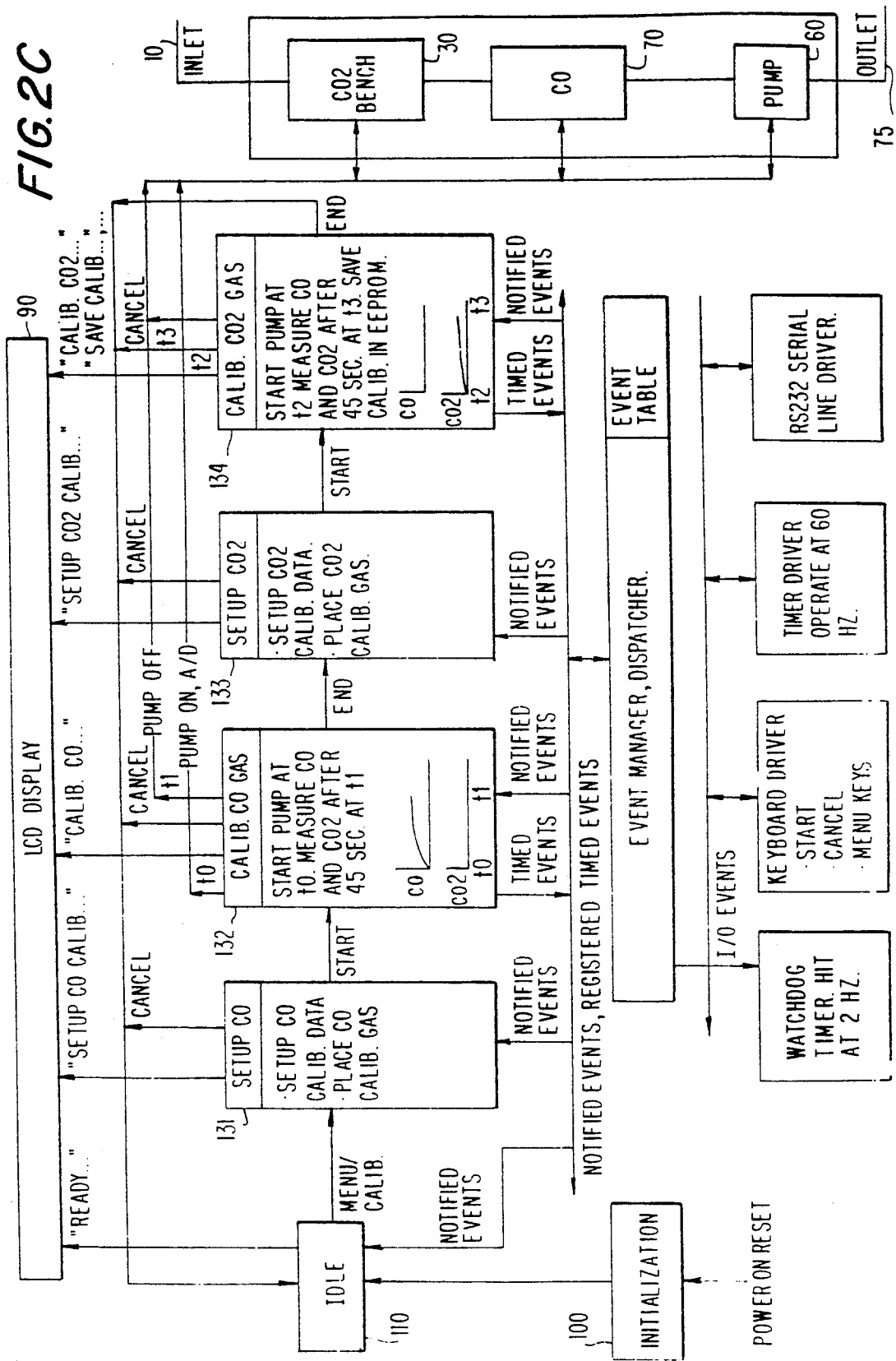

IN-VIVO MEASUREMENT OF END-TIDAL CARBON MONOXIDE CONCENTRATION APPARATUS AND METHODS

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

This invention relates to methods and apparatus for in-vivo, real time measurement of end-tidal carbon monoxide concentration in the exhaled breath, more particularly the determination of end-tidal carbon monoxide concentration in the breath of a newborn infant.

BACKGROUND OF THE INVENTION

In most animal systems, carbon monoxide is a waste product produced in the breakdown of free hemoglobin within the blood. Ordinarily, hemoglobin is contained within red blood cells and is stable. However, aging of red blood cells and certain disease processes produce hemolysis, i.e., the breakdown of the cell wall. This produces free hemoglobin which breaks down in the blood. The carbon monoxide that is produced by the breakdown of free hemoglobin is normally excreted in the breath.

When the system is in equilibrium, the carbon monoxide concentration in the breath is proportional to the difference in the concentration of carbon monoxide in the blood and the concentration of carbon monoxide in room air. This difference in concentration is proportional to the rate of hemolysis in the blood.

The concentration of carbon monoxide in the end-tidal breath, i.e., the gas that is last expelled each breath, is presumed to be at equilibrium with the concentration in the blood. This is because the end-tidal breath contains predominantly, if not exclusively, the gas expelled from the alveoli in the lungs, which gas was within the alveoli for a time generally sufficient to equilibrate with the blood.

It is known that hemolysis and the resulting by-products and consequences of hemolysis can be estimated or predicted from a measure of the concentration of carbon monoxide in the end-tidal breath. See Smith, D. W. et al., "Neonatal Bilirubin Production Estimated from End-Tidal Carbon Monoxide Concentration", *Journal of Pediatric Gastroenterology and Nutrition*, 3:77-80, 1984.

One method of analysis previously reported includes incrementally acquiring a sample of end-tidal breath and analyzing the acquired sample by mass spectroscopy or gas chromatography to determine the end-tidal carbon monoxide concentration. The sample is obtained by extracting from each of several successive breaths a portion of the apparent end-tidal breath using a syringe. The end-tidal portion of breath is determined by observing the chest movements of the infant. See, e.g., Vreman et al. U.S. Pat. No. 4,831,024.

One problem With this technique is that it requires a skilled, trained user to obtain the end-tidal sample in successive increments based on watching chest wall movements. It also requires a trained, skilled person to operate a complex piece of analytical laboratory equipment to analyze the acquired sample. In addition, this technique requires time and personnel to transport the sample from the patient to the laboratory (or equipment) where the analysis is conducted, and then to report back to the attending physician/practitioner for a diagnosis and prescription, if any.

Another problem with this technique is that accurate assessment of the concentration difference in carbon monoxide requires obtaining good samples of end-tidal patient breath. This essentially requires that the patient have a regular, predictable breathing cycle. Thus, it can be difficult to obtain a good sample by watching chest wall movement, particularly for a newborn and for patients having irregular breathing cycles.

Chemical electrochemical sensors capable of measuring carbon monoxide concentrations in the range of interest, 0 to 500 parts per million (ppm), are commercially available, e.g., model DragerSensor CO available from Dragerwerk, Lubeck, Germany. However, such sensors are sensitive to many other gases as well as carbon monoxide, and are therefore susceptible to error. Another problem with such sensors is that the measurement dynamics of the sample gas transport through the gas permeable membrane and oxidation-reduction in the electrochemical cell results in a relatively slow response time such that discrete samples of the end-tidal breath must be obtained and analyzed to determine the end-tidal carbon monoxide concentration.

SUMMARY OF THE INVENTION

It is, therefore, an object of the present invention to provide improved non-invasive apparatus and methods for measuring carbon monoxide concentration in the end-tidal breath. It is another object to provide apparatus and methods that operate in real-time. It is another object to provide apparatus and methods for use in determining the rate of hemolysis from the concentration of end-tidal carbon monoxide.

It is another object of the present invention to provide apparatus and methods for measuring end-tidal carbon monoxide that do not require a highly skilled, trained individual to obtain and determine the measure. It is another object to provide such apparatus and methods that do not require incrementally acquiring samples of end-tidal breath during successive respiratory cycles.

It is another object of the invention to provide a portable, easy-to-use apparatus that can be used in a nursery, a physician's office, a hospital, a clinic, and a mobile clinic for measuring end-tidal carbon monoxide in real-time, for assessing the likelihood of elevated levels of hemolysis for immediate entry on the patient's record and prescription of an appropriate remedy.

In accordance with this invention, there is provided an apparatus, sampling methods, and analysis techniques for measuring the concentration of end-tidal carbon monoxide in breath, particularly in newborn and premature infants. Broadly, the invention concerns determining the concentration of end-tidal carbon monoxide based on a measure of the room air carbon monoxide concentration, a measure of the average carbon monoxide concentration for a breath sample over a period of time, and a determined ratio of the end-tidal breath to inspired air for the sampled portion.

The present invention is based in part on the discovery that accurate assessment of end-tidal carbon monoxide concentration may be obtained based on knowledge of the fraction of the gas sample that is end-tidal gas. Thus, the present invention is able to avoid selectively sampling small samples of end-tidal breath over successive respiratory cycles to obtain a sufficiently large end-tidal breath sample, which incremental sampling is problematic. Further, the invention advantageously uses a conventional carbon monoxide detector, which has a response time that is not fast enough to distinguish carbon monoxide in end-tidal breath from carbon monoxide in inspired air, to derive the end-tidal carbon monoxide concentration in real-time. More particularly, a conventional carbon monoxide detector can be used to obtain the average carbon monoxide concentration level during breathing, which average value can be related to the end-tidal value based on the determined ratio of end-tidal to inspired breath. Preferably, the most common interfering substances from a sampled breath are removed from the sample by a consumable filtration medium so that these substances do not affect the measurement. The present invention also applies to gas components of exhaled breath other than carbon monoxide, which gas components cannot be directly monitored because of the slow response time of available gas detectors.

One aspect of the present invention concerns using a second gas component of the breath, other than the first gas component whose concentration is being monitored, to determine the ratio of the end-tidal breath to inspired air. The relative concentration level of the second gas during respiration is monitored and the ratio or duty cycle of the end-tidal portion of the sensed concentration waveform relative to the inspired air is determined. A sensor for detecting the level (or concentration) of the second gas having a time response that is fast enough to distinguish the end-tidal breath concentration from the inspired air is preferably used. One suitable gas component is carbon dioxide, which has a large, distinctive change in concentration with breathing. Other gases may be used, e.g., hydrogen, oxygen, or some combination of gases, e.g., carbon dioxide and hydrogen.

The determined end-tidal carbon monoxide concentration may be used by a physician or other suitable health care provider to evaluate the rate or relative level of hemolysis occurring in the infant. The evaluation is typically made by comparing the determined end-tidal carbon monoxide concentration to known or preselected standards. For example, when measured soon after birth, the end-tidal carbon monoxide range 0.6-1.9 $\mu l/l$ is considered normal and the range above about 2 $\mu l/l$ is considered at risk. Premature infants have both a higher risk of neonatal jaundice and a higher normal range of end-tidal carbon monoxide.

The present invention provides a tool for predicting the likelihood that the determined level of hemolysis will lead to adverse consequences, such as jaundice and hyperbilirubinemia, which might not appear for several days. Thus, the apparatus and methods of the present invention provide for reliable detection and early treatment of the condition by an appropriate remedy, and for monitoring the efficacy of the treatment.

BRIEF DESCRIPTION OF THE DRAWINGS

The above and other objects and advantages of the invention will be apparent upon consideration of the following detailed description taken in conjunction with the accompanying drawings, in which like reference characters refer to like parts throughout, and in which:

FIGS. 2A-2D are macro flow diagrams for the overall, breath measurements, calibration, and data communication operations of the apparatus of FIG. 1;

DETAILED DESCRIPTION OF THE INVENTION

Figure 1:
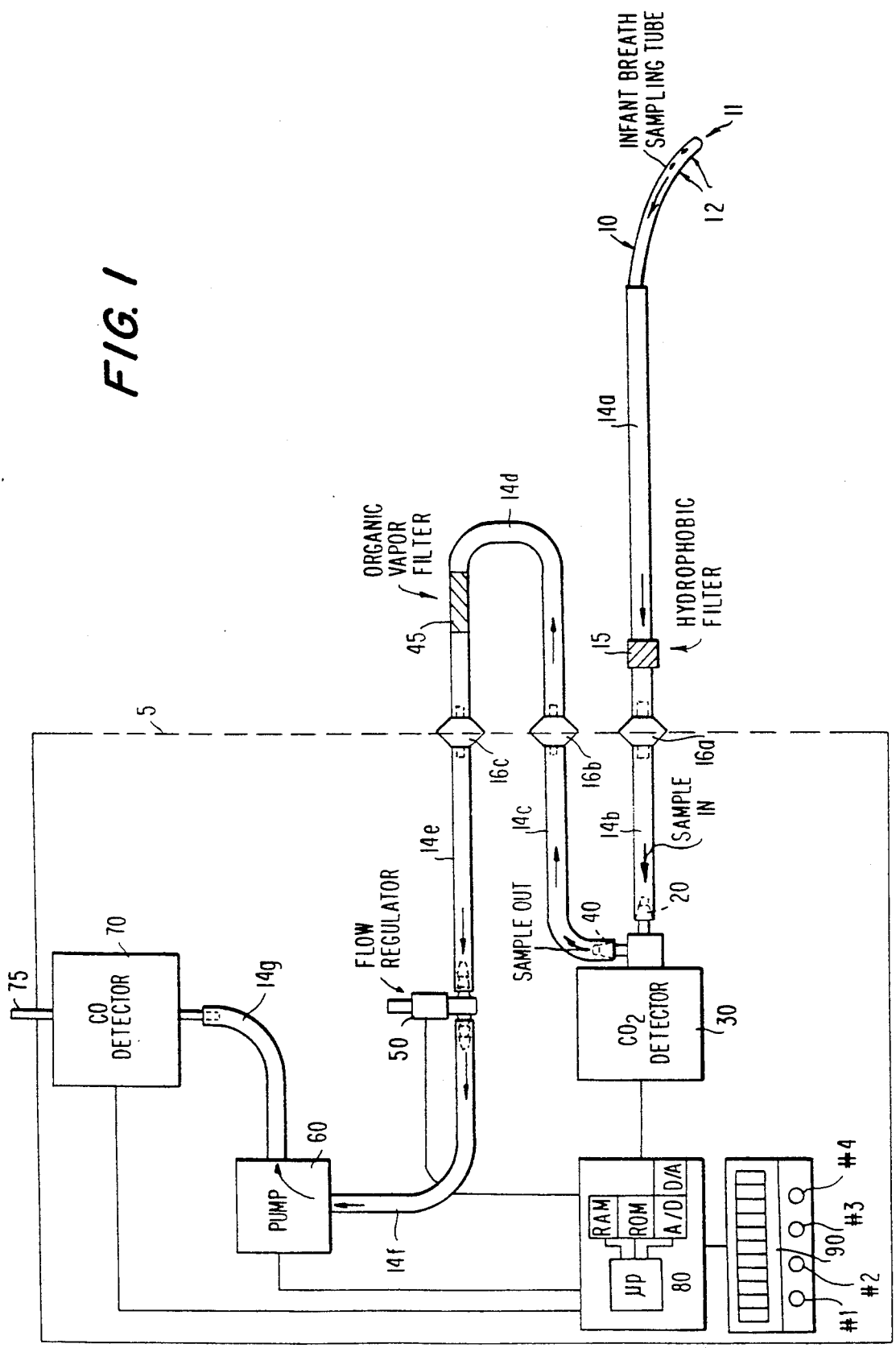
FIG. 1 is a schematic block diagram of an apparatus for determining end-tidal carbon monoxide concentration in accordance with the present invention.

Referring to FIG. 1, a preferred embodiment of the present invention relates to methods and apparatus for monitoring breath flow of a patient over a period of time and determining the end-tidal concentration of carbon monoxide in the breath. The apparatus includes a nasal cannula 10, a carbon dioxide detector 30, an organic vapor filter 45, a flow regulator 50, a pump 60, a carbon monoxide detector 70, and a microcontroller 80. Preferably, a hydrophobic filter 15 is provided between the cannula 10 and the gas detectors to remove moisture from the sample of breath. In particular, filter 15 is used so that moisture does not interfere with detecting carbon dioxide. Filter 15 is illustrated in FIG. 1 as inserted between tube 14a, which includes cannula 10, and a connector 16a, which is secured to the base 5 which supports and preferably encloses the gas detectors 30 and 70, pump 60, and flow regulator 50. One suitable hydrophobic filter 15 is part number 51190, available from Filtertek, Inc.

Cannula 10 is one segment of tubing 14a which has one end 11 that is adapted for insertion into the nostril (posterior nasal pharynx) of a normally breathing patient, e.g., an infant. End 11 has at least one aperture 12 for extracting a sample of the exhaled breath as described below. Preferably, end 11 has a length and an inner and outer diameter appropriate for insertion into the patient's nostril, e.g., a 3.0 cm length of tubing having an inner diameter on the order of 1.0 to 1.5 mm and an outer diameter of 2-3 mm, and a sufficient number of holes 12 perforating the tube circumference for receiving a sample of breath. The dimensions may be adjusted for the size of the patient. The length of cannula 10 is sufficient to extend from the base 5 to the patient, and is typically on the order of 75 to 100 cm.

Segments of tubing 14a, 14b, 14c, 14d, 14e, 14f and 14g are used to form the flow path between the various elements of the apparatus as shown in FIG. 1. The tube segments may be made of, for example, medical grade catheter tubing, polyethylene, polypropylene or vinyl. The ends of the segments are typically frictionally fitted over bosses of connectors 16 and the various components as shown in FIG. 1 and may be clamped for a more secure interconnection. Connectors 16a, 16b, and 16c are preferably mounted in the same region of base 5 to allow for easy access for replacement of the cannula and filters.

Cannula 10 is connected at its other end in series with filter 15, connector 16a, a second length of tubing 14b and the input port 20 of a carbon dioxide detector 30. Detector 30 has a gas sample cell and is used to provide a signal corresponding to the sensed concentration of carbon dioxide in the gas. The detector 30 has a response time that is sufficiently fast to distinguish the concentration level of the end-tidal portion from the other portions of the breath. Thus, the signal changes in response to changes in the concentration of carbon dioxide in the breath as the patient breathes. The resultant signal waveform is used, as described below, to determine the ratio of the end-tidal portion of the breath to the entire inspired air. This ratio, referred to as the duty cycle ("dc") is used to convert the detected carbon monoxide concentration ("CO") to the end-tidal carbon monoxide concentration ("$CO_{ET}$"), as described below.

One suitable carbon dioxide gas analyzer is the commercially available Servomex model 1505 fast response carbon dioxide infrared transducer, which is available from Servomex Company, 90 Kerry Place, Norwood, Mass. 02062. This device is a temperature compensated, sealed transducer that is based upon a single beam, single wavelength technique absorption for measuring carbon dioxide. It has a complete optical bench and uses a fast infra-red carrier which is attenuated by the infrared absorption of carbon dioxide in the gas. The device has detection circuitry that will convert fast changes of attenuation into an electrical output signal.

The Servomex model 1505 transducer is used in accordance with the manufacturers directions and specifications. It provides, under constant conditions, a linear output voltage of from 0 to 1.0 volts corresponding to from 0 to 10% carbon dioxide, and is extendable up to 1.5 volts corresponding to 15% carbon dioxide. The response time is on the order of 120 ms at a flow of 100 ml/min, and the flow rates may be in the range of from 50–200 ml/min. Other carbon dioxide measuring devices also could be used.

Figure 5:
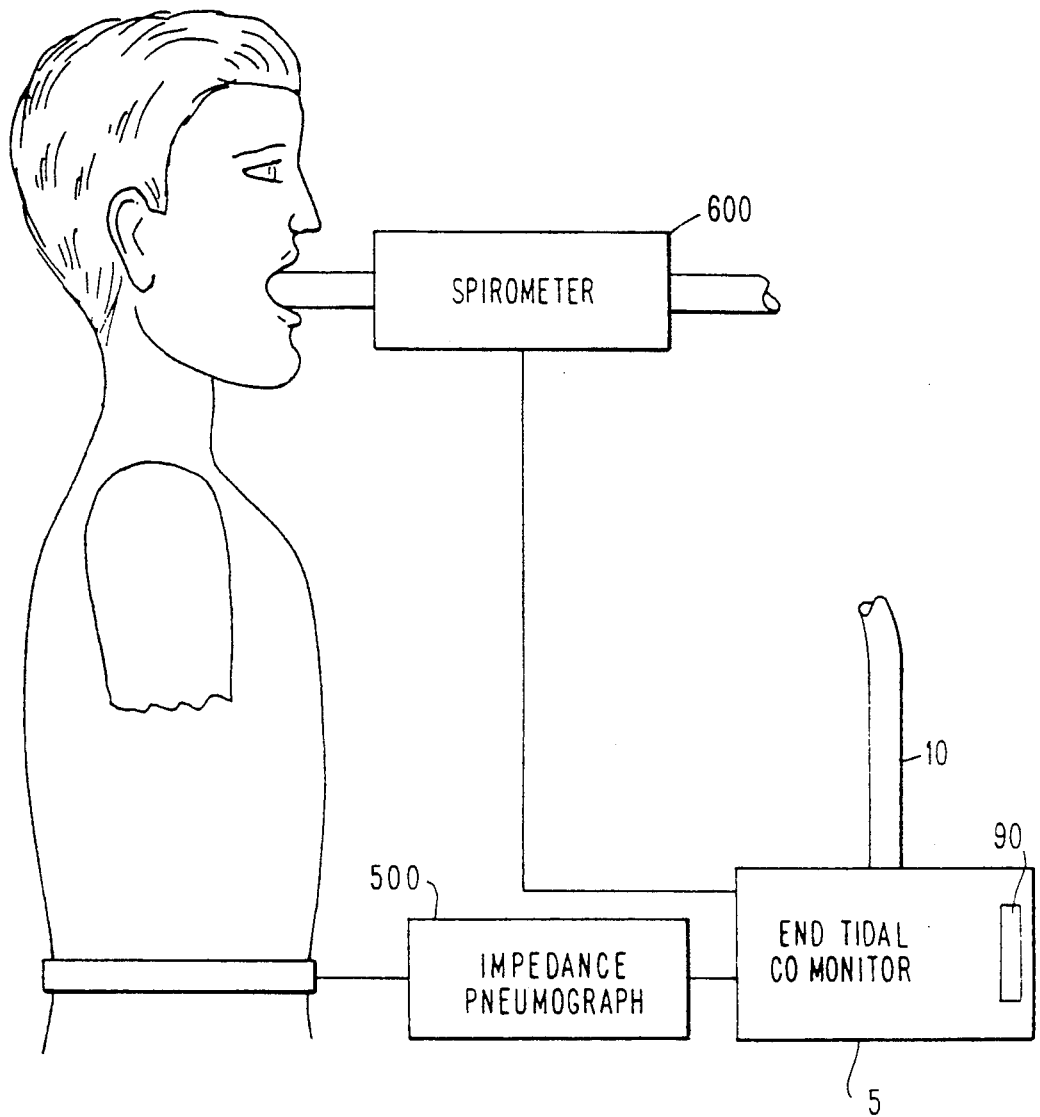
FIG. 5 is a schematic block diagram of an apparatus for determining end-tidal carbon monoxide concentration in accordance with alternate embodiments of the present invention.

It should be understood that any device that is capable of determining the duty cycle of end-tidal breath to inspired air over a given period of time may be used in place of the carbon dioxide detector, provided that the determined duty cycle is for the same period of time during which the sample on which the carbon monoxide concentration determination is based was acquired. Such a device may be a spirometer 600 for measuring flow velocity or flow volume, a non breath flow device 500 for monitoring breathing, e.g., an impedance pneumograph, a microphone sensor, and the like. See FIG. 5, which shows the conventional locations of spirometer 600 and an impedance pneumograph type non flow breath monitor 500, the latter of which surrounds the patient's body to produce a signal that varies as the patient's body varies with breathing. Also, a breath gas detector for monitoring a breath gas other than carbon dioxide may be used.

The carbon dioxide detector is preferred because changes in $CO_2$ concentrations related to end-tidal flow are relatively large and easily detectable using a threshold level of carbon dioxide. Further, the same sample of breath can be used to determine the carbon monoxide and carbon dioxide concentrations without affecting the sample, particularly when the sample stream is passed through an infrared absorption-type carbon dioxide detector prior to an electrochemical cell type carbon monoxide detector. In addition the use of an exhaled gas (carbon dioxide or another) provides a non intrusive and non invasive technique for determining the duty cycle dc. It does not require an additional or alternate sensor or transducer on or near the patient and it does not require additional patient cooperation or discomfort. Furthermore, using one time-sample of breath to determine the duty cycle of end-tidal breath is more accurate than visually monitoring chest wall movement or respiratory activity over a period of breathing cycles, or relying on a predetermined breathing rate, which are subject to change, and attempting to obtain samples of exhaled breath only during end-tidal portions.

Other gas sensors may be used, e.g., oxygen which would have a relatively reduced concentration level during end-tidal breath, or hydrogen, which would have a relatively increased concentration level during end-tidal breath. Two different gas detectors, e.g., carbon dioxide and hydrogen, could be used to identify the end-tidal portion, wherein carbon dioxide provides a fast response and hydrogen provides a slow response to changes in concentration.

Another advantage of the invention with respect to relying on changes in gas concentration levels is that the measurement decouples the breath gas concentrations from rhythmic respiratory activity. In other words, pump 60 may be used to provide a gas flow rate through cannula 10 and the flow path that is greater than the patient's respiratory flow. This, in turn, provides an end-tidal "waveform" stretching that enhances evaluation of the gas concentrations and determination of the end-tidal portion of the breath based on a breath gas. It also provides for synchronization between the respiratory activity corresponding to the end-tidal portion based on carbon dioxide and the detection of carbon monoxide concentration in the same breath sample flow. Consequently, the carbon monoxide concentration may be calculated based on post data acquisition processing analysis of the last acquired sample. As a result, the end-tidal carbon monoxide determination is effectively provided in real-time and without the delay occasioned by the previously reported techniques. In addition, the present invention avoids reliance on a previously established breathing cycle or rate to predict when chest wall movement coincides with end-tidal flow. Instead, the invention is completely responsive to changes in the patient's breathing rate and volume as the sample is acquired. The prior known techniques are not.

The gas flow output 40 of detector 30 is in turn connected to a piece of tubing 14c and passed through connector 16b into tube segment 14d. Tube segment 14d contains an organic vapor filter 45. Filter 45 may contain any medium that will absorb organic vapors and reducing gases that might interfere with detecting carbon monoxide levels in the carbon monoxide detector 10.

Filter 45 preferably contains activated charcoal. It is preferably constructed as a canister that either can be inserted interior to the flow path of tube 14d or is inserted between two segments of tubing such that the analyte gas stream passes through the canister. Filter 45 illustrated in FIG. 1 connected between two connectors 16b and 16c so that it is external to base 5. This provides for simple and quick replacement of filter 45 when it is substantially consumed. Filter 45 may be an inexpensive disposable portion of the apparatus.

One advantage to using filter 45 is that it tends to average the concentrations of gas in the analyte stream by thoroughly mixing the stream within the volume of filter 45. A preferred construction of filter 45 is to use a 20 mm length of charcoal rod having a circumference of 24.4 mm which is sandwiched between 3.0 mm segments of white acetate having the same circumference. The charcoal rod is preferably cut from Filtrona AAD Charcoal Filter Rods, available from American Filtrona Corp., Richmond, Va. Where desired, more than one carbon rod segment may be used, provided that pump 60 has sufficient power to pass the analyte gas stream therethrough.

Flow regulator 50 and pump 60 are inserted, preferably in tandem as illustrated in FIG. 1, into or between segments of tubing 14 to maintain a desired constant flow velocity of the analyte stream. Flow regulator 50 is interposed between tubing 14e, which is connected to connector 16c, and tubing 14f, which is connected to pump 60. Pump 60 is in turn interposed between tubing 14f and tubing 14g, which is connected to carbon monoxide detector 70.

Preferably, pump 60 and flow regulator 50 are adjusted so that the flow is maintained at from 40 to 60 ml/min, more preferably 50 ml/min. This provides for withdrawing continuously a gas sample, either from room air or from the patient's posterior nasal pharynx, depending on placement of the cannula 10, including expired and end-tidal breath for patients having a breathing rate of from 10 to 90 breaths per minute. The flow regulator 50 provides for limiting the flow rate of the analyte gas stream, and the pump 60 provides for sampling the gas sample (room air or breath) such that pump 60 is driven against the flow rate limit set by flow regulator 50. This maintains a constant flow rate for the analyte stream, and avoids any flow surges due to a patient's inhalation or expiration. One suitable flow regulator is orifice/needle valve model F-2822-41-B80-55 available from Air Logic, Racine, Wis., which can be adjusted to obtain the desired gas flow rate in the range of 40–60 ml/min. One suitable pump is model NMP 02 diaphragm micro pump, available from KNF Neuberger, Inc, Princeton, N.J., which has a free flow capacity of 0.22 to 0.55 L/min. Pump 60 and flow regulator 50 may be located anywhere in the flow stream, preferably between the carbon dioxide detector 30 and carbon monoxide detector 70 inside the enclosure of base 5. Pump 60 also passes the analyte flow stream out exhaust 75, downstream of the gas detectors 30 and 70 of the apparatus.

Carbon monoxide detector 70 is preferably an electrochemical sensor that produces an electrical current proportional to the concentration of reducing gases, such as carbon monoxide, which are present in the gas at the gas permeable membrane of detector 70 (not shown). The response time of the carbon monoxide detector 70 and the averaging function of the filter 45 preferably result in a signal output from the detector 70 that is proportional to the average concentration of the reducing gas at the membrane.

One suitable carbon monoxide sensor is model DragerSensor CO, available from Dragerwerke of Lubeck, Germany. It has a plastic gas permeable membrane, a liquid electrolyte, sensing, reference, and counter electrodes in the electrolyte, and a potentiostatic circuit that maintains a constant voltage between the sensing and reference electrodes. The carbon monoxide in the gas is electrochemically converted at the sensing electrode, which produces a current proportional to the carbon monoxide partial pressure. The device is temperature compensated. It has a concentration sensitivity in the range up to 500 ppm and provides an output current of $0.13 \pm 0.4$ $\mu$A/ppm, and requires about 20 seconds to equilibrate fully with the gas sample being monitored; it has a reaction half life of ten seconds.

Microcontroller 80 is used to control the operation of the apparatus. Microcontroller 80 receives signals related to the output signals from carbon dioxide detector 30 and carbon monoxide detector 70, corresponding to the sensed instantaneous carbon dioxide concentration and sensed average carbon monoxide concentration, respectively. These received signals are processed to compute a value corresponding to the end-tidal carbon monoxide concentration in the patient's breath, as described below. The computed value may then be displayed on a display 90, such as a liquid crystal display device.

Preferably, a conventional digital microcontroller system is used having a suitable software-controlled microprocessor, memory, analog to digital conversion, and signal conditioning functions. Of course, as will be apparent to persons of ordinary skill in the art, discrete analog circuit elements and solid state finite state machines also may be used to control the operation of the elements and obtain the concentration measurement.

One suitable digital microcontroller is the model Little Giant LG-X miniature microcontroller, available from Z World Engineering, Davis, Calif. The microcontroller 80 is connected to carbon dioxide detector 30, carbon monoxide detector 70, pump 60, and flow regulator 50 (if one is used) to operate and/or receive signals from those devices. An amplifier interface circuit 82 is used to provide for current to voltage conversion of the signals provided by carbon monoxide detector 70.

Figure 2:
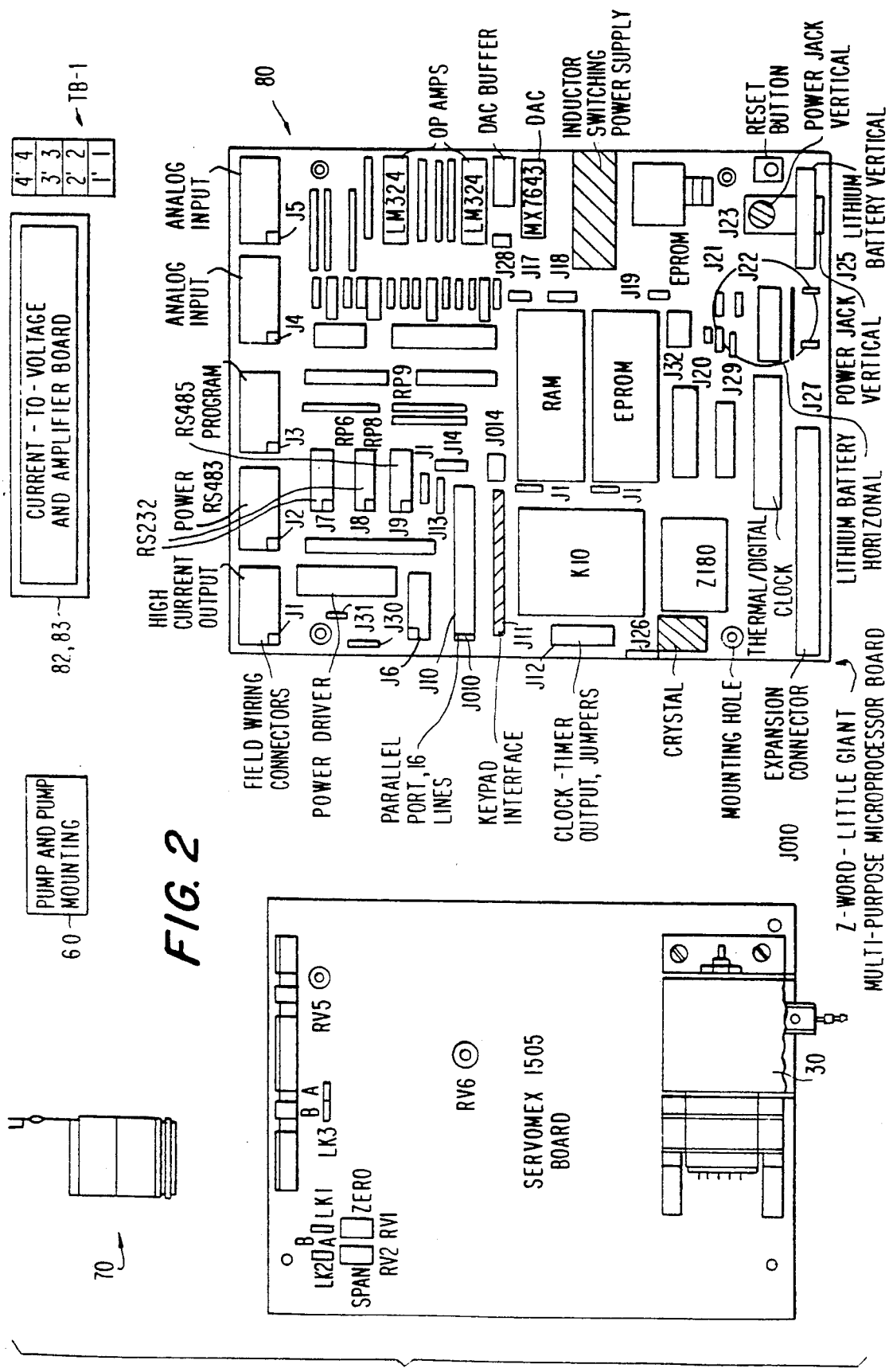
FIG. 2 is a diagram of a multipurpose microcontroller board for controlling the device in FIG. 1.
Figure 2B:
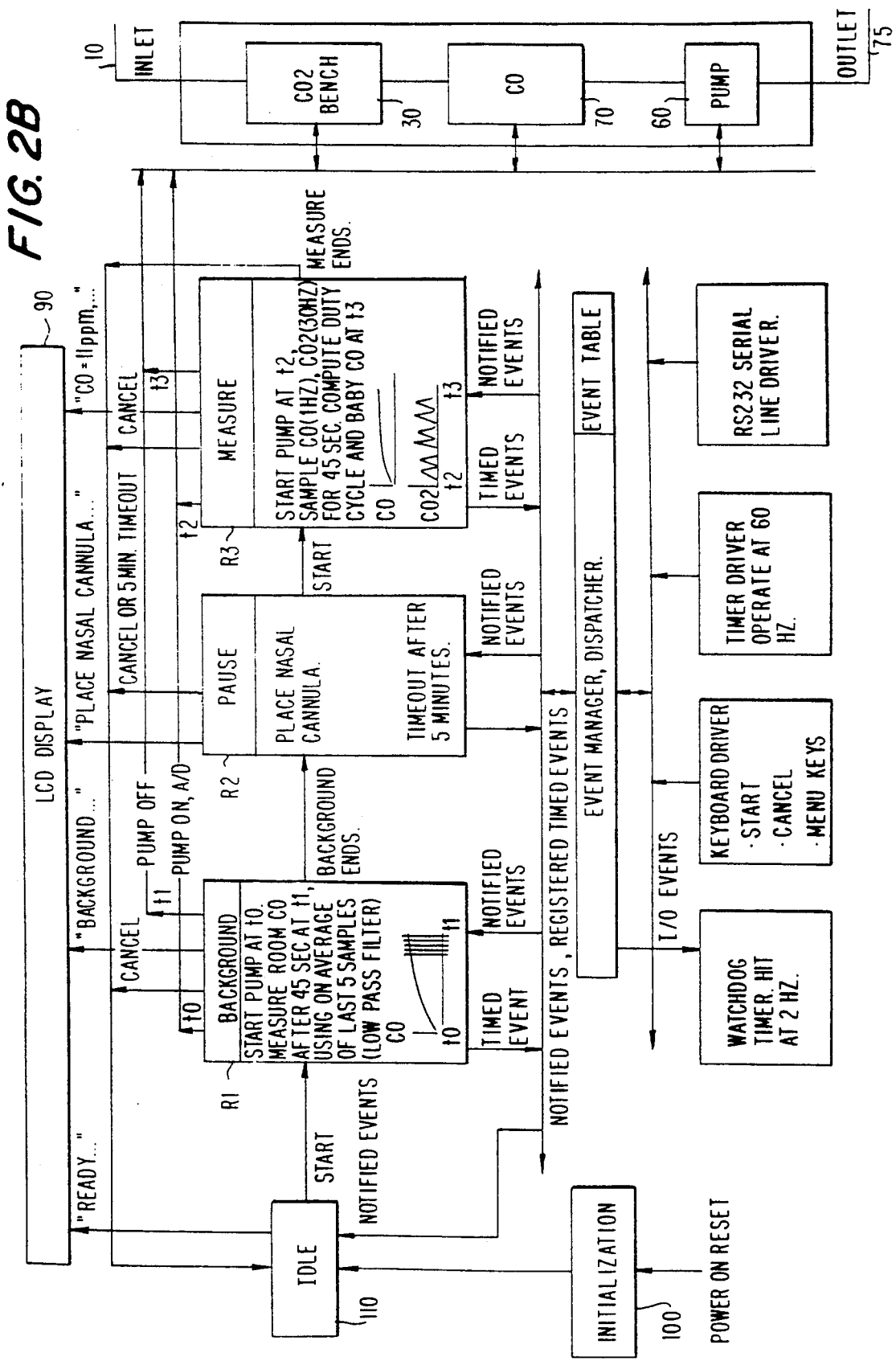
Figure 2D:
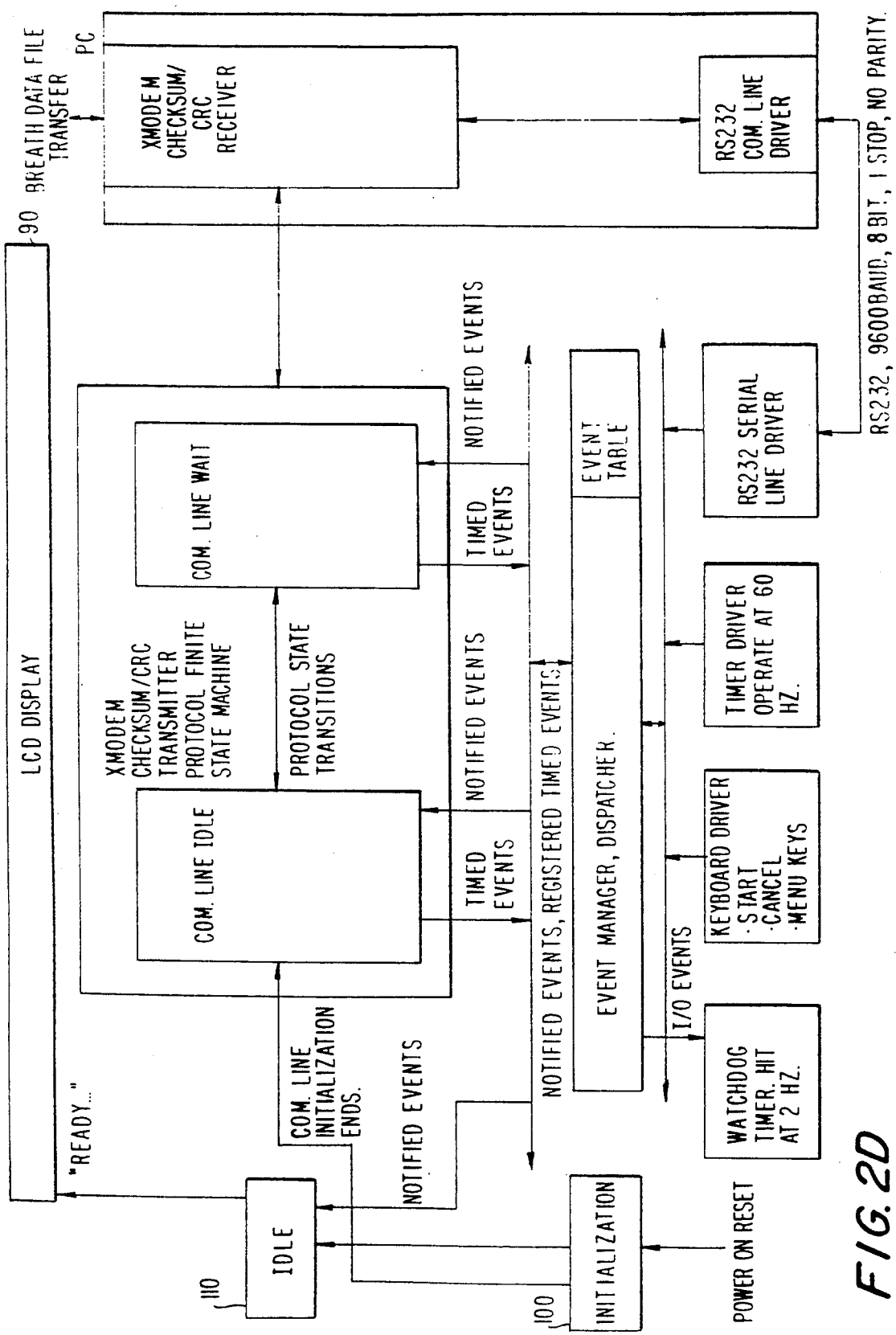
Figure 2E:
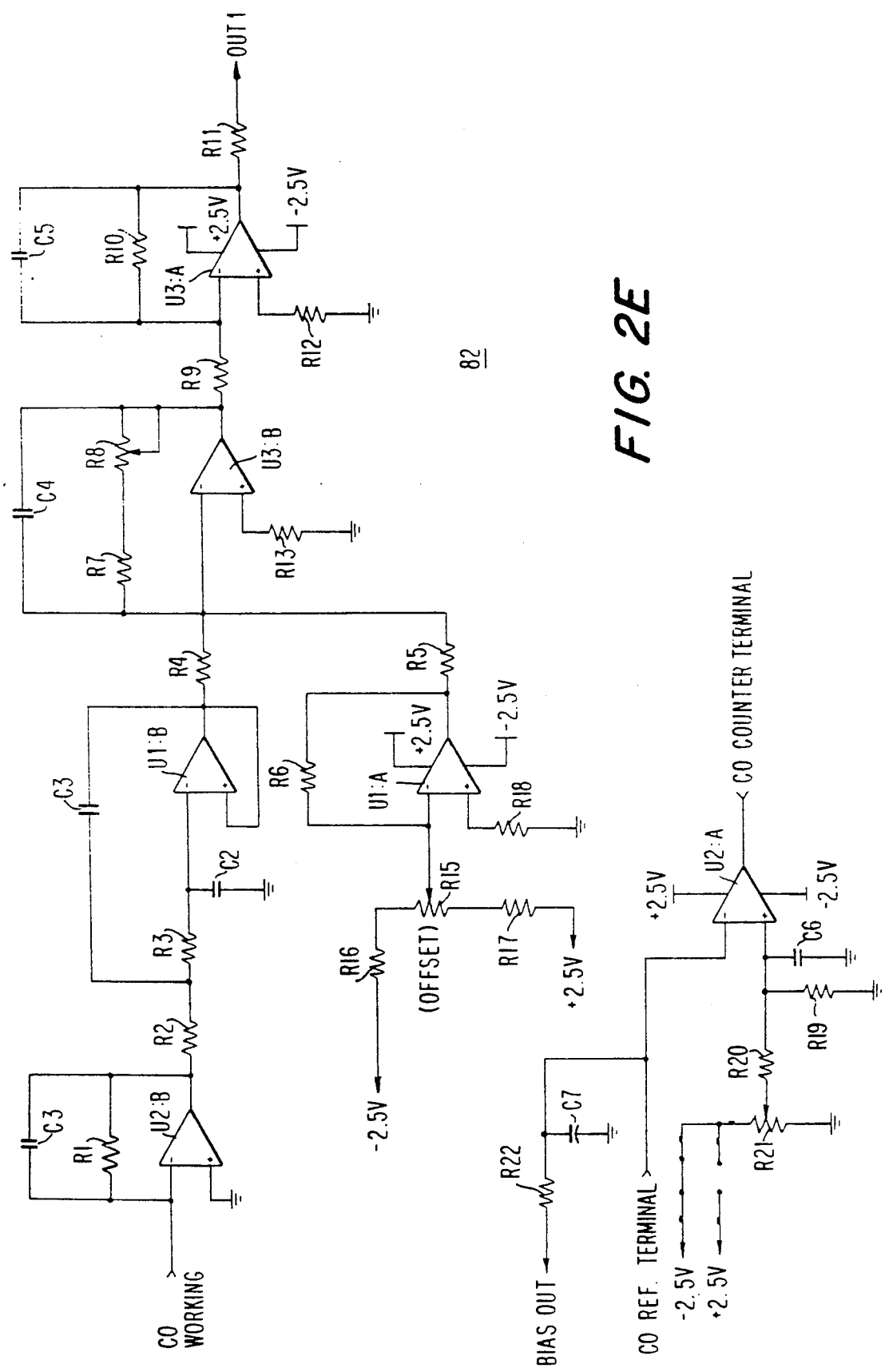
FIGS. 2E and 2F are circuit schematic diagrams for a signal conditioning amplifier and a power supply respectively, for interfacing the carbon monoxide sensor of FIG. 1 and the microcontroller circuit board of FIG. 2.

Referring to FIG. 2E, interface circuit 82 includes three amplifiers, U1B, U2B and U3B, which are preferably OP-290 low-noise, dual operational amplifiers available from Precision Monolithics, Inc., Santa Clara, Calif. Amplifier U2B is configured as a current to voltage converter, having a 0.1 $\mu$f capacitor C3 in parallel with a 50 k$\Omega$ resistor R1 in the feedback loop. The gain is determined by resistor R1.

Amplifier U1B is a second order lowpass filter with approximately a 0.5 second time constant, using two 470 k$\Omega$ resistors R2 and R3 and two 1 $\mu$f capacitors C2 and C3 configured as shown. The filter is used to attenuate electrical noise.

Amplifier U3B is configured as a simple amplifier with gain adjustment potentiometer R8 (100 K$\Omega$) in series with a 10 k$\Omega$ resistor R7, both of which are in parallel with a 0.1 $\mu$f capacitor C4 in the feedback loop, and a 10 k$\Omega$ input resistor R4 at the inverting amplifier input. Potentiometer R8 is used to allow initial calibration to compensate for sensitivity variations in gas detectors. Amplifier U3B also has a secondary input from amplifier U1A, which is configured as an adjustable voltage source that may be used to compensate for a zero gas output of detector 70.

Amplifier U3A is configured as a unity gain buffer designed to isolate the previous stages from any load effects that may imposed by following circuitry.

Amplifier U2A is configured as shown as an adjustable bias source for the counter electrode of detector 70.

as determined by the setting of resistor R21, a 500 kΩ potentiometer. A 10 ,Ω resistor R22 provides a means of reading the bias voltage without making direct contact with the gas detector connections. The CO detector amplifier circuit 82 operates as a low power supply voltage to prevent excess leakage currents from imposing undesirable bias currents on the detector 70, and to allow low power continuous biasing of the detector 70 to allow for stable operation. Preferably, amplifiers U2A and U3A also are type OP-290 amplifiers. In the circuits illustrated in FIGS. 2E and 2F, all ground connections are to a virtual ground, which is provided by a CO amplifier power supply circuit 83.

Figure 2F:
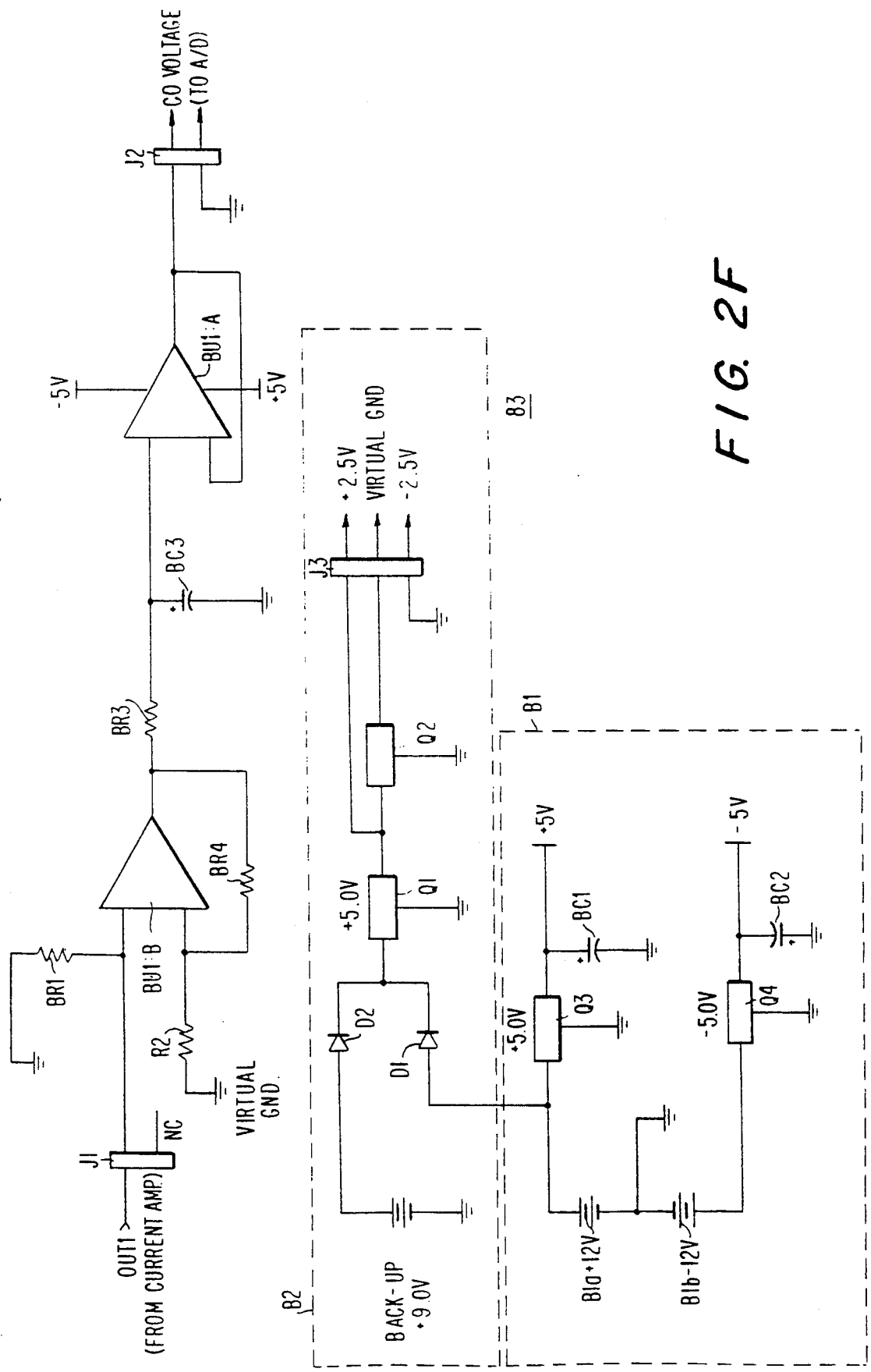

Referring to FIG. 2F, the CO amplifier power supply and interface circuit 83 is shown. The power supply consists of a normal supply B1 and a backup supply B2. Normal supply B1 may be any nominal +/−12 volt DC power supply. In one preferred embodiment, normal supply B1 is a regulated power supply derived from AC mains. Alternately, two 12 volt batteries, e.g., rechargable batteries, could be used.

Devices Q3 and Q4 are integrated circuit regulators (types LM78L05 and LM79L05) with provide +/−5 volts respective, for powering the interface amplifier BU1A. Diodes D1 and D2 (IN4148 type diodes) automatically switch to supply to the CO amplifier BU1A the greater of the normal 12 volt DC supply B1a, and the backup battery B2, an alkaline 9 volt battery.

Device Q1 regulates the supply voltage to +5 volts. Device Q2 is an integrated circuit virtual ground supply, model TLE2425, available from Texas Instruments, Dallas, Tex. Its output "splits" the five volt input into a ±2.5 volt supply with a virtual ground at 2.5 volts DC "real" potential.

Amplifier BU1 of circuit 83 includes two type 1458 dual operational amplifiers, BU1A and BU1B, available from National Semiconductor, Santa Clara, Calif. Amplifier BU1B is configured as a differential amplifier with gain of 1, and has inputs of the virtual ground from the CO amplifier circuit 82 and the CO amplifier circuit 82 output. Resistors BR3 (120 kΩ) and capacitor BC3 (10 μf) provide further low pass filtering with a 1.2 second time constant. Amplifier BU1A is configured as a voltage follower with a low output impedance, for driving the analog input on the Little Giant microcomputer board 80.

Referring to FIG. 2, the Little Giant LG-X microcontroller 80 is programmable using Z-World's Dynamic C language. It uses about 200 mA, contains a microprocessor Z180 having a 9.216 MHz clock frequency and sufficient memory including read only memory ROM, random access memory RAM, and erasable, programmable read only memory EPROM, which collectively contain the software, data, and memory address locations for operating the apparatus, processing the acquired data, and performing the data manipulation and post acquisition processing functions in accordance with the present invention, as described herein. The device also contains counter-timers, including a 2 Hz watchdog timer for automatically resetting the microprocessor in the event of undefined operations or temporary power loss, serial input/output ports, parallel input/output ports, time and date clocks, multi-channel analog to digital converter, a digital to analog converter, operational amplifiers for input signal conditioning in single ended or double ended modes, adjustable gain and input voltage ranges, a high current driver output suitable for driving pump 60, and other particular elements provided by the manufacturer which either are used in a conventional manner although not pertinent to the present invention, or are not used. The microcontroller is used in accordance with the manufacturer's directions and specifications, except as otherwise noted, and reference is made to the user manual for the device, entitled "Little Giant Single Board Computer Technical Manual Version E" which is available from the manufacturer, for information regarding configuring and implementing use of the microcontroller.

The display device 90 is capable of providing a display corresponding to the determined carbon monoxide concentration level in the end-tidal breath $CO_{ET}$. Preferably, display 90 includes a display screen for alphanumeric text, including the determined $CO_{ET}$ concentration, and preferably instructions to the operator for operating the device to acquire the appropriate gas samples. Further, display device 90 is preferably user-interactive and includes both a keyboard for operator input and a visual display for prompting the operator to act. Also, the display device 90 may include a paper printer or have an associated printer (not shown) for providing a printed copy of the parameters determined and/or measured, in character text or graphic form. Alternately, or in addition, audible sounds, visual indicators or lights may be used to prompt the operator to perform the appropriate act.

One suitable display device is a model LG-LCD keypad liquid crystal display device, available from Z World Engineering. This device has definable function keys on a keyboard and a visual character display. The visual display includes a 2 line by 16 character LCD. The keyboard has a 4 x 4 keypad and a beeper for keypad feedback. It is compatible with and directly interfaces with the Little Giant LG-X miniature microcontroller.

Referring to FIG. 2, a printed circuit board layout of the Z World Little Giant microcontroller circuit board is illustrated and the interconnection of elements is described, using the manufacture's conventional pin connections (unless otherwise stated). Referring to terminal board TB1, one or more AC-DC regulated power supplies (not shown) are used to provide the following signals to the four numbered input pins of terminal TB1: −12 volts to pin 1, ground potential to pin 2, +5 volts to pin 3, and +12 volts to pin 4. The corresponding four output pins of terminal board TB1, designated TB1-X' wherein "X" refers to the output pin, are respectively connected in series with the input pins of TB1 and the pins of the apparatus illustrated in FIG. 1 as follows.

Regarding microcontroller 80, the high current output wiring connectors J1 have pin J1-8 connected to the negative terminal of pump 60 for providing a current to drive pump 60 at the selected rate. There are no other connections for wiring connectors J1. The power wiring connectors J2 have pin J2-1 connected to J2-4, pin J2-2 connected to J2-3, pin J2-6 connected to TB1-2'(ground), pin J2-7 connected to TB1-4'(+12 v), and no other J2 pin being connected. The RS485 field wiring connectors J3 are not used in this embodiment.

The analog input field wiring connectors J4 have pins J4-1 and J4-2 connected to amplifier interface board pins J2-1 and J2-2 respectively, pin J4-3 connected to pin PL4-1 on the Servomex 1505 board, and pin J4-4 connected to pin PL4-2 on the Servomex model 1505 board. Analog input pins J5, RS232 port pins J7, and RS485 program pins J9 are not used. The pins at keyboard interface J6 are used to connect a flat ribbon cable to the back panel of the display 90, LCD display device model LG-LCD. The pins J8 for the RS232 port are connected on the back panel to a conventional nine pin D-sub connector. The display 90 interface pins J10 are connected as follows. Pin J10-10 are the common front panel buttons; pin J10-12 is for button #1, pin J10-14 is for button #2, pin J10-16 is for button #3, and pin J10-18 is for button #4.

Regarding the Servomex model 1505 circuit board, it is connected as follows. For device Power, pin PL1-1 is connected to TB1-1' (−12 v), pin PL1-2 is not connected, pin PL1-3 is connected to TB1-2' (ground), pin PL1-4 is connected to TB1-3' (+5 v). For device Thermistor Status, pins PL2 are not connected. For device Nitrous Oxide Compensation, pins PL3-1 and PL3-2 are jumpered and no other pins are connected. For device Signal Output, pins PL4-1 is connected to Little Giant pin J4-3 and pin PL4-2 is connected to Little Giant board J4-4. For device Remote Calibration Adjustment, there are no pin connections.

According to a preferred embodiment of the present invention, the end-tidal carbon monoxide concentration of the patient is measured in the following manner. An initial value of carbon monoxide may be obtained for analysis purposes. Pump 60 is then started and a sample of room air is drawn through the segments of tubing 14a-14g at the selected flow rate of, e.g., 50 ml/min, past the carbon dioxide detector 30 and the carbon monoxide detector 70. At the end of a first time period, e.g., 45 seconds, the measures of the concentrations of the carbon dioxide and carbon monoxide in the sample cells of the carbon dioxide sensor 30 and carbon monoxide sensor 70 are obtained, respectively. The measures are obtained as analog signals from the detectors 70 and 30, e.g., sensed currents converted to conditioned voltages $v_{CO}$ and $v_{CO2}$, which are respectively digitized into n-bit words (n is preferably 8) at selected sampling rates and passed into a data buffer and/or memory. The values are stored as $CO_{room}$ and $CO_{2zero}$.

Pump 60 is then turned off and the cannula 10 is placed in the patient's nostril, preferably in the posterior nasal pharynx. Then the pump 60 is turned on again and an analyte stream of breath is drawn past the respective gas detectors 70 and 30. The concentrations of carbon monoxide and carbon dioxide are respectively sensed and sampled during a second time period, e.g., 45 seconds.

The acquired measures of the carbon dioxide concentration over the second time period are evaluated. First, the relative changes in the carbon dioxide concentration are evaluated to determine the duty cycle corresponding to the end-tidal portion of the patient's breath. An average of the end-tidal CO, concentration ("$CO_{2ET}$") to the average $CO_2$ is obtained, providing the duty cycle dc.

The end tidal CO concentration ("$CO_{ET}$") is then determined from the following relationship:

$$CO_{ET} = [CO_{mean} - CO_{room}]/dc \tag{1}$$

where $CO_{mean}$ is the average or mean carbon monoxide concentration at the end of the second period, and dc is the duty cycle determined for $CO_{2ET}$.

Referring to FIG. 1, the macro flow diagrams of FIGS. 2A to 2D, and the software appendix attached hereto, a preferred embodiment of the operation of the present invention is now described. In this embodiment, display device 90 is configured to use four buttons which are used for controlling the operation of the apparatus. Button #1 is a start button to initiate some action by the apparatus to reset the apparatus operation, button #2 is a reset button, button #3 is a select button to select some option from a menu, and button #4 is a menu button to display one or more instruction and/or operation menu. Each button is activated by pressing in and then releasing the button. Other alternatives for providing user input in an interactive device may, of course, be used.

Referring to FIG. 2A, the device becomes activated on power on or reset (pressing button #2) and enters an initialization sequence at step 100. During initialization, the operating code of microcontroller 80 is booted and various system checks and device initializations are performed. Following initialization, the routine passes to an idle state at step 110, where it waits for user input. During the idle state, the system preferably generates a suitable message on display 90, e.g., "Ready, press 1 to start". Thus, during the idle step 110, the user may provide an input by pressing button #1 to start a measuring sequence. This passes the operating routine to step 120.

Also during the idle state 110, the operator may press button #3 to select a sequence from a menu displayed on the display unit 90, and button #4 to display various operation sequences. One such sequence is a calibration routine for calibrating the carbon monoxide detector 70 and carbon dioxide detector 30 at step 130. The operator also may press button #2 at any time to exit whatever routine it is executing, reset the apparatus, and return the routine to step 100.

Referring to FIGS. 2A and 2B, in response to pressing button #1 in the idle state 110, the routine moves from the idle step 110 to step 120 for the sequence for determining end-tidal carbon monoxide concentration $CO_{ET}$. There are three phases to this determination, a sequence at step 121 for measuring the background carbon monoxide $CO_{room}$ during a first time period, a pause or delay period at step 122, and a sequence at step 123 for measuring breath carbon dioxide $CO_2$ and carbon monoxide CO during a second time period.

In the present invention, before each sample is obtained, pump 60 is off for a delay time period. This allows the CO detector to return to a zero state so that effectively no CO is in the sample cell. When desired, a supply of inert gas may be provided and pump 60 activated for a time to clear the sample cell of any CO (and $CO_2$) gas. A three-way valve and an actuator may be included (not shown) to achieve this cell clearing function. The delay time period is at least about one minute, more preferably three minutes.

In the background measurement sequence step 121, the user is prompted to place the end 11 of cannula 10 somewhere in the vicinity of the patient, but not inside the nostril and then to press button #1. In response to pressing button #1, pump 60 is activated at time $t_0$ and the background room air is drawn through tubing 14 and during a first time period of approximately 45 seconds. During this time, display 90 preferably displays a suitable message corresponding to the duration of the background measuring test, e.g., how much time remains to complete the test, in seconds or in percent.

At time $t_1$ at the end of the first time period, pump 60 is turned off. The carbon monoxide concentration in the sample cell of the carbon monoxide detector 70 is then determined and recorded in memory as $CO_{room}$. As noted, the carbon monoxide gas detector has a time response to the analyte flow that produces an average carbon monoxide concentration. As set forth in the software appendix hereto, the digitized samples corresponding to the carbon monoxide concentration are processed so that the output signal is the average of the last five acquired samples. Preferably the determined concentration value is displayed, e.g., in parts per million (ppm). The amplitude of the voltage signal $v_{CO}$, corresponding to the averaged sensed carbon monoxide concentration $CO_{room}$ from detector 70 that is displayed, also may be displayed for diagnostic purposes.

The CO and $CO_2$ gas equations used to convert the sampled voltage signals corresponding to the detector signal outputs to gas concentrations are:

$$CO\ ppm = m_1 v_{CO} + c_1 \tag{2}$$

$$CO_2\% = m_2 v_{CO2} + c_2, \tag{3}$$

where $m_1$ and $c_1$ are the slope and intercept calibration constants relating the voltage $v_{CO}$ derived from the CO detector 70 output in response to the concentration of carbon monoxide in a sample to ppm, and $m_2$ and $c_2$ are the slope and intercept calibration constants relating the voltage $v_{CO2}$ derived from the $CO_2$ detector 30 output in response to the carbon dioxide concentration in a sample, in percent.

Thus, at time $t_0$, with CO=0 ppm, using the above equation:

$$0 = m_1 v_{CO} + c_1 \text{ and} \tag{2.1}$$

$$c_1 = m_1 v_{CO-0} \tag{2.2}$$

where $v_{CO-0}$ corresponds to the signal produced by CO detector 70 at time $t_0$. At time $t_1$, $$\begin{aligned} CO_{room}\text{ppm} &= m_1 V_{CO-1} + c_1. & (2.3) \\ &= m_1 V_{CO-1} - m_1 V_{CO-0} & (2.4) \\ &= m_1 (V_{CO-1} - V_{CO-0}) & (2.5) \end{aligned}$$

where $v_{CO-1}$ corresponds to the signal produced by CO detector 70 at time $t_1$.

When pump 60 is stopped at time $t_1$ at the conclusion of the background step 121, the CO is measured and the routine enters pause step 122. During the pause step 122, the operator is prompted to place the nasal cannula 10 inside the patient's nostril and then to press button #1 to resume the measurement sequence. The system preferably displays a suitable message on display 90, e.g., "place nasal cannula", to prompt the user to place the cannula 10. The pause step 122 preferably includes a minimum delay period Timeout of about ten seconds and a maximum delay period Timeout of about five minutes. Thus, if the operator does not press the start button #1 within the Timeout period, the system will return to the idle state 110. The Timeout period is used to provide for sampling the room air and patient carbon monoxide concentrations within a time period wherein it is not likely that the room air concentration level will change very much. The Timeout period also is selected to permit the operator sufficient time to insert the nasal cannula 10 in a patient, such as a newborn infant, which may require some time to accomplish.

Once the cannula 10 is place, the operator presses button #1 to resume the measurement sequence 123. At time $t_2$, pump 60 is turned on for a second time period, which is preferably the same as the first time period, i.e., 45 seconds. Initial CO and $CO_2$ samples may be obtained for analytical purposes. During this second time period, the display 90 preferably displays a suitable message corresponding to the duration of the measuring test, e.g., how much time remains to complete the test, in seconds or in percent. At time $t_3$, at the end of the second time period, pump 60 is turned off.

During the second time period, the signals corresponding to the $CO_2$ concentration obtained from $CO_2$ detector 30 are acquired. The relative changes in $CO_2$ concentration over time are then used to calculate the duty cycle dc of the patient's end-tidal breath. Preferably, the signal corresponding to the carbon dioxide concentration is periodically sampled, e.g., the analog signal is digitized at a first sampling rate, e.g., 30 Hz during the second time period. These samples are stored in a data buffer for post data acquisition processing and analysis.

Also, the signals corresponding to the CO concentrations obtained from detector 70 are acquired during the second time period. Preferably, the carbon monoxide concentration is periodically sampled, e.g., the analog signal is digitized at a sampling rate of 1.0 Hz during the second time period. These samples also are stored in the data buffer for analysis.

Figure 3A:
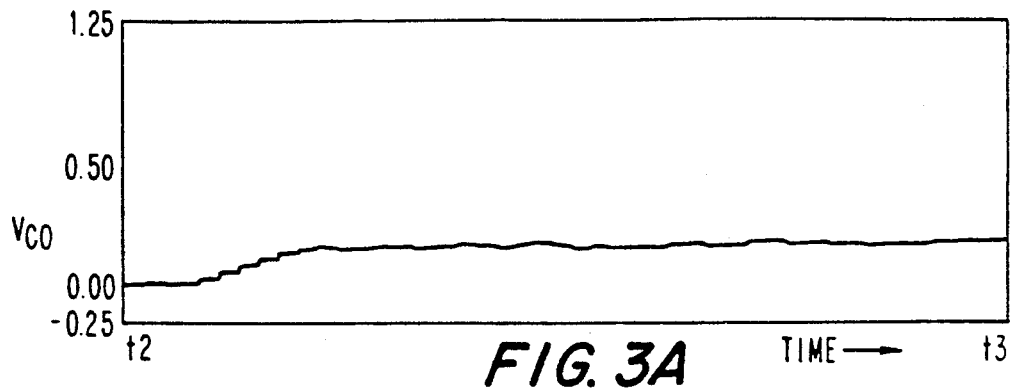
FIGS. 3A and 3B are graphical illustrations of measurements of carbon monoxide carbon dioxide concentrations acquired using the device of FIG. 1.
Figure 3B:
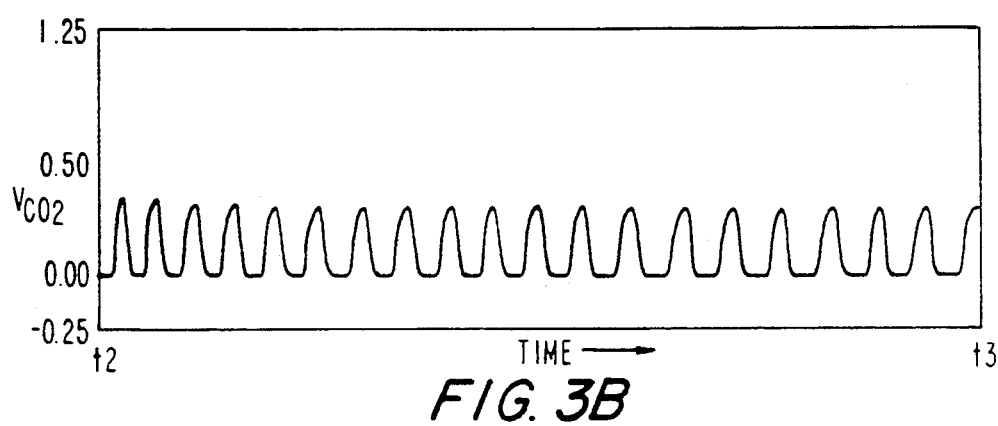

FIGS. 3a and 3b illustrate representative sampled waveforms of the signals $v_{CO}$ and $v_{CO2}$ provided by the CO and $CO_2$ detectors 70 and 30 respectively, during a second time period. The waveforms thus display the concentration levels sensed corresponding to the calibrated CO and $CO_2$ levels. In these representative drawings, the calibration functions were:

$$CO\ ppm = 12.11\ v_{CO} + 0.95; \text{ and}$$

$$CO_2\% = 11.96\ v_{CO2} + 0.$$

The calculated duty cycle dc was 42.30%, the $CO_{ET}$ was 2.10 ppm, the $CO_{ROOM}$ was 2.01 ppm, the $v_{CO-0}$ was $-0.78$ v and the $v_{CO-1}$ was 0.088 v. The $v_{CO}$ min was $-0.05$ v and the $v_{CO}$ max was 0.17 v (corresponding also to the start ($t_2$) and stop ($t_3$) measurement voltages). The maximum $v_{CO2}$ was about 0.42 volts.

The 30 Hz sampling rate of $CO_2$ was selected because it corresponds to the anatomical waveform of respiration from which the ratio of the end-tidal portion to the total air can be derived. The $CO_2$ sensor time response of 120 ms gives adequate resolution without acquiring excessive data. The sampling rate of 1 Hz for the CO detector voltage $V_{CO}$ was selected because the CO detector has a much slower response time (the half time of the CO response is about ten seconds) which cannot discriminate the end-tidal portions and room air. Sampling at a higher rate would not significantly improve the data resolution. The selected rates were selected as compromises between collecting sufficient data with adequate resolution in view of the sensor response time, and may be changed according to the sensors used and the particular conditions of use.

Following acquisition of the data, the data is processed by the microprocessor Z180 of microcontroller 80 to derive the duty cycle dc and the end-tidal CO concentration $CO_{ET}$. The digitized samples of the voltage $v_{CO}$ are passed through a low pass digital filter, implemented in the software, which takes an average of the last five samples. This filter is used to suppress noise. It also advantageously permits use of the output of the digital filter without further averaging or storage of separate values. The corresponding average or mean CO concentration at time $t_3$, $CO_{mean}$, is thus $$CO_{mean} = m_1 V_m + c_1. \quad (4)$$

where $V_m$ is the average of the last five voltage samples $v_{CO}$.

The duty cycle dc is calculated based on analysis of the sampled voltages $v_{CO2}$ between time $t_2$ and $t_3$, as follows:

$$dc = \frac{[\text{the number of CO}_2 \text{ samples} > V_t]}{[\text{total number of CO}_2 \text{ samples}]}$$

$$= \frac{[\text{the number of CO}_2 \text{ samples} > 1.5\%]}{[\text{total number of CO}_2 \text{ samples}]}$$

where $V_t$ is a selected threshold voltage corresponding to, e.g., a 1.5% $CO_2$ concentration, and is obtained from the $CO_2$ gas equation (3) as follows:

$$1.5\% = m_2 V_t + c_2,$$

$$V_t = (1.5 - c_2)/m_2.$$

For an ideal $CO_2$ detector 70, $m_2 = 10$ and $c_2 = 0$, such that $V_t = 0.15$ volts. Of course, other values and threshold voltages could be used as appropriate in the particular circumstances.

Then, the patient's end-tidal CO concentration $CO_{ET}$ is:

$$CO_{ET} = (CO_{mean} - CO_{room})/dc. \quad (1)$$

This may be calculated in a straightforward manner from the acquired data.

Figure 4A:
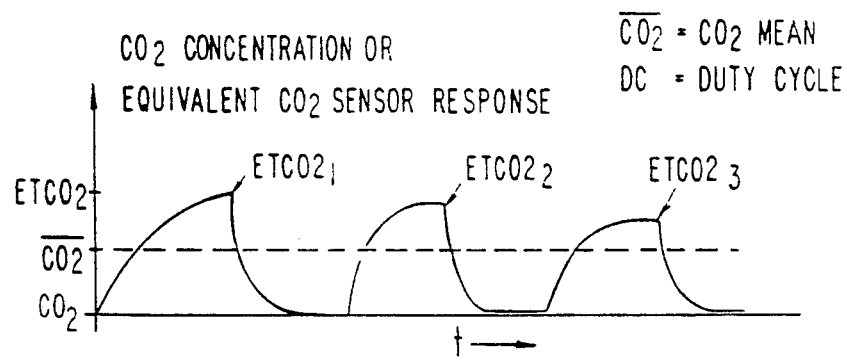
FIGS. 4A and 4B are graphical illustrations of the carbon monoxide and carbon dioxide concentrations in a representative breath flow.
Figure 4B:
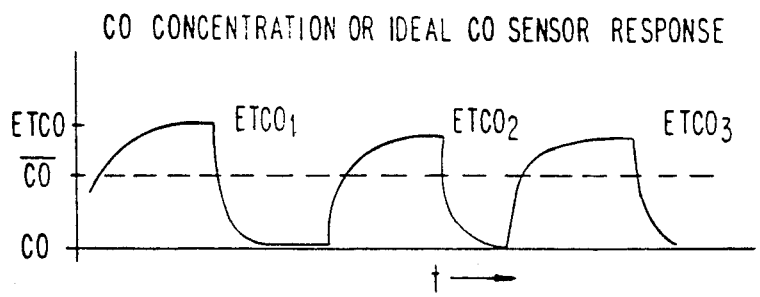

The foregoing equations are based on the realization that the physical behavior of CO and $CO_2$ are very similar with respect to, for example, diffusion, flow rates and other behavior characteristics in the patient's cardiopulmonary system. Accordingly, it can be assumed that ratio of the end-tidal $CO_2$ portion to the total $CO_2$ portion is the same as the ratio of the end-tidal CO portion to the total CO portion. This is illustrated in FIGS. 4a and 4B. Further, it can be assumed that the $CO_2$ concentration of room air is approximately 0 and that the end-tidal $CO_2$ concentration is related to the duty cycle of the breath waveform and the mean value of the $CO_2$ concentration, namely:

$$CO_{2ET} \cdot dc = CO_{2mean}. \quad (5)$$

Thus, based on these assumptions, the CO and $CO_2$ ratios are $$\frac{CO_{2ET} - CO_{2room}}{CO_{2mean} - CO_{2room}} = \frac{CO_{2mean}/dc - 0}{CO_{2mean} - 0} = \frac{CO_{ET} - CO_{room}}{CO_{mean} - CO_{room}}$$

and thus $$1/dc = \frac{CO_{et} - CO_{room}}{CO_{mean} - CO_{room}} \quad (6)$$

and the total end-tidal $CO_{ET}$ is $$CO_{ET} = \frac{(CO_{mean} - CO_{room})}{dc} + CO_{room} \quad (7)$$

Therefore, to obtain the patient's actual end-tidal CO level produced, the portion of the patient's breath from the $CO_{room}$ concentration (i.e., the CO level that was inhaled by the patient) must be subtracted from the total, which yields the equation (1) above.

The determined values are then displayed on display 90 and any desired printouts of the acquired data may be made or stored to a memory device or medium for subsequent analysis, as desired. The routine then exits the measuring sequence 120 and returns to the idle state at 110. The display preferably include the determined $CO_{ET}$, e.g., in ppm, and also may provide the duty cycle of the carbon dioxide waveform corresponding to the end-tidal portion, and/or various voltages from the detectors 30 and 70, such as minimum and maximum voltages corresponding to CO and $CO_2$, and initial and final voltages for $CO_{mean}$ and/or $CO_2$ during the second time period. It is noted that, in connection with the second time period for monitoring the patient's breathing, the time references $t_0$ and $t_1$ may be used in place of time references $t_2$ and $t_3$ respectively.

Preferably, the data from the measurement cycle just finished will remain displayed for a period of time to allow the operator to record manually the data. The display 90 may be cleared by pressing button #1 (or reset #2). Following measurement of a sample, the aforementioned delay time period of about one minute (or three minutes) is provided to allow the CO and $CO_2$ detectors 70 and 30 to decay to a "zero" state before the next background measurement cycle begins. Preferably, any attempt to obtain another measurement before the end of the delay period will be simply delayed until the expiration of that time, and then automatically commence.

Referring to FIGS. 2A and 2C, the CO and $CO_2$ detectors 70 and 30 are periodically calibrated using conventional CO and $CO_2$ gases having known concentrations. To begin the calibration sequence 130, the system must be in the idle state 110. The operator then presses button #4 to call the menu up on display 90. The menu will display an appropriate message such as "menu 1. Calibrate CO/CO2 sensor. Activate button #1 to start". The operator then presses button #1 which begins the calibration sequence 130. The calibration sequence involves the selection of test gases of known concentrations, inputting the known concentration values into the system during set-up sequence 131 for CO and set-up sequence 133 for $CO_2$, operating the pump 60 to draw the known gas into the system and determining the signal level produced by the detector (30 or 70 depending on the gas; only one detector is calibrated at a time) in response to the known gas concentration during measurement sequence 132 for CO and measurement sequence 134 for $CO_2$.

In a preferred embodiment, the display 90 is used to provide a sequence of instructions for the operator to input data, such as which gas detector is to be calibrated and the concentration of the test gas that is to be used (sequences 131 and 133). This is followed by providing a sample of that test gas, which is then sampled and measured (sequences 132 and 134). Preferably, at least two gas samples at different known concentrations are used for each of CO and $CO_2$. From these two samples, the foregoing gas calibration equations (2) and (3) for converting a provided voltage to a gas concentration are determined. The calibration equations are reasonably accurate over the concentration ranges of interest, e.g., accurate within 10%.

In one embodiment, in sequences 131 and 133, a keyboard associated with display 90 may be used to input the test gas type and concentration data directly by pressing alphanumeric characters. In accordance with a preferred embodiment using the Little Giant LCD display device, select button #3 is used to toggle a digit that is underscored on the display screen menu between values, to display the known gas concentration value. The menu button #4 is used to move the underscore along the displayed characters for selecting the character to be changed. Start button #1 is used to indicate that the character now displayed is the correct value, which value is then stored for use in deriving the calibration function for the gas detector being calibrated. The calibration is thus conducted in a known manner and preferably produces a linearized calibration function.

Preferably two samples of each gas at known concentrations are used. Thus, two points are obtained, (v1, p1) and (v2, p2), where v1 and v2 are the measured voltages and p1 and p2 are the corresponding known gas concentrations. Using these two test points, the calibration constants are conventionally obtained as follows:

$$m = (p2 - p1)/(v2 - v1) \tag{8}$$

$$c = (p1\ v1 - p2\ v1)/(v2 - v1). \tag{9}$$

Referring to FIG. 2D, a macro flow diagram of the data communication function of the apparatus is shown. Initialization step 100 provides for initialization of the communications channel. This channel establishes serial RS-232 communication under the industry standard x-modem protocol with external devices, such as portable computers. It is used to monitor the operation of the gas analyzer and for development and diagnosis of system failures. Any terminal device such as a portable computer equipped with a suitable communication program such as BITCOM, or PROCOMM, will automatically be able to receive the data files at 9600 baud for the examination and evaluation.

Set forth as a software appendix hereto is a program code listing of software, written in Z World Dynamic-C language, for operating the Little Giant multipurpose microcontroller and the Little Giant LG-LCD display device, and the above-identified CO and $CO_2$ detectors and pump. Implementation of the present invention in alternate microprocessor controlled devices, analog circuit controlled devices, and finite state machines with appropriate controlling software, integrated and/or discrete circuit elements and logic circuits, is believed to be within the ability of a person of ordinary skill in the art.

One advantage of the present invention that it provides a simple and easy-to-use device that accurately and relatively quickly obtains a measure of the end-tidal carbon monoxide concentration of a patient. The determination is made immediately following acquisition of the breath sample and is thus performed in real-time. It overcomes the above-noted problems of the prior art techniques. The present invention is particularly useful for detecting abnormal levels of hemolysis in newborn and premature infants, as well as determining incipient hyperbilirubinemia, elevated levels of bilirubin, the likelihood of the onset of jaundice, and the resolution of those conditions over time. Importantly, with respect to newborn and premature newborns, it provides for enhanced detection of potential problems before the newborns are discharged from the hospital.

One skilled in the art will appreciate that the present invention can be practiced by other than the described embodiments, which are presented for purposes of illustration and not of limitation.

I claim:

1. Apparatus for monitoring a patient's end-tidal gas flow during breathing comprising:
   a first gas detector for monitoring the concentration of a first selected gas in a gas sample and having an output corresponding to the monitored first selected gas concentration;
   a first means for monitoring a parameter corresponding to the patient's breathing and determining the ratio of said parameter corresponding to the patient's end-tidal breath portion to said parameter corresponding to inspired air as a duty cycle and having an output corresponding to the determined duty cycle;
   first means for providing a sample of room air to the first gas detector for measuring a background concentration of the first gas;
   second means for providing a sample of the patient's breath to the first gas detector for measuring a breath sample concentration of the first gas in the patient's breath; and
   first means for receiving the output of the first gas detector and the first monitoring means for determining a end-tidal concentration of the first gas in response to the determined duty cycle, the determined background concentration of the first gas in room air, and the determined breath sample concentration of the first gas in the patient's breath.

2. The apparatus of claim 1 wherein the first gas is carbon monoxide, the first gas detector detects the concentration of carbon monoxide and the first receiving and determining means determines the end-tidal concentration of carbon monoxide.

3. The apparatus of claim 1 wherein the first monitoring and determining means further comprises:
   a second gas detector for monitoring an concentration of a second selected gas in the patient's breath other than the first selected gas and having an output corresponding to the second selected gas concentration; and
   second means for receiving the output of the second gas detector and for determining the duty cycle as the ratio of the end-tidal portion of the second gas in the patient's breath to the patient's breath based on monitored relative changes in the sensed concentration of the second gas.

4. The apparatus of clam 3 wherein the second gas detector further comprises a carbon dioxide gas analyzer.

5. The apparatus of claim 3 wherein the second providing means further comprises means for passing the sample of the patient's breath to the first and second gas detectors wherein the second gas detector monitors changes in the concentration of the second gas in the patient's breath over time.

6. The apparatus of claim 5 wherein the passing means further comprises a pump and a flow path, the flow path connecting the first and second gas detectors in gaseous communication and the pump passing a gas sample therethrough.

7. The apparatus of claim 6 wherein the second providing means turns the pump on for a selected first time period.

8. The apparatus of claim 6 wherein the first providing means turns the pump on for a first selected time period and the first gas detector detects the room air concentration of the first gas.

9. The apparatus of claim 8 wherein the second providing means turns the pump on for a second selected time period following the end of a first time period.

10. The apparatus of claim 8 wherein the first providing means turns the pump on for on the order of forty-five seconds and wherein the second providing means turns the pump on for on the order of forty-five seconds.

11. The apparatus of claim 7 wherein the second receiving and determining means further comprises:
   first means for periodically sampling the output of the second gas detector corresponding to the sensed concentration of the second gas during the first selected time period; and
   comparator means for comparing the sampled signals to a selected threshold;
   wherein the second receiving and determining means determines the duty cycle based on the sampled signals that are above and below the selected threshold.

12. The apparatus of claim 11 wherein the second receiving and determining means determines the duty cycle based on the number of sampled signals above the selected threshold.

13. The apparatus of claim 12 wherein the second receiving and determining means determines the duty cycle based on the ratio of the number of samples above the threshold and the number of samples.

14. The apparatus of claim 11 further comprising
   second means for periodically sampling the output of the first gas detector corresponding to the sensed concentration of the first gas during the first selected time period; and
   means for providing a first signal corresponding to an average of a selected number of sampled second signals near the end of the first period.

15. The apparatus of claim 14 wherein the first time period is on the order of 45 seconds, the first sampling means samples the second gas detector output on the order of 30 Hz, the second sampling means samples the first gas detector output on the order of 1.0 Hz, and the selected number of sampled second signals is on the order of 5.

16. The apparatus of claim 14 wherein the first gas detector is a carbon monoxide gas analyzer and the second gas detector is a carbon dioxide gas analyzer.

17. The apparatus of claim 11 wherein the first gas detector is a carbon monoxide gas analyzer and the second gas detector is a carbon dioxide gas analyzer.

18. The apparatus of claim 5 wherein the first gas detector is a carbon monoxide gas analyzer and the second gas detector is a carbon dioxide gas analyzer.

19. The apparatus of claim 2 wherein the first gas detector detects the room air carbon monoxide concentration in response to the first providing means and an average concentration of carbon monoxide in the patient's breath in response to the second providing means.

20. The apparatus of claim 19 wherein the first receiving and determining means determines the end-tidal carbon monoxide concentration based on the room air concentration, the average concentration, and the duty cycle.

21. The apparatus of claim 1 further comprising an interactive keyboard and display associated with the first and second providing means.

22. The apparatus of claim 1 wherein the second providing means provides a sample of the patient's breath for a first time period so that the first gas detector provides a signal corresponding to an average concentration of the first gas.

23. The apparatus of claim 1 wherein the first means for monitoring breathing further comprises an impedance sensor for coupling the patient for sensing changes in impedance with the patient's respiratory activity.

24. The apparatus of claim 1 wherein the first means for monitoring breathing further comprises a spirometer.

25. A method of measuring end-tidal carbon monoxide concentration in expired breath comprising the steps of:
   (a) measuring a carbon monoxide concentration in ambient room air ($CO_{room}$);
   (b) sampling a patient's breath over a first period of time;
   (c) measuring the carbon monoxide concentration (CO) in a sampled patient's breath during the first time period;
   (d) determining a duty cycle of an end-tidal portion of the patient's breath during the first time period; and
   (e) determining an end-tidal carbon monoxide level based on the determined duty cycle, the measured $CO_{room}$, and the measured CO.

26. The method of claim 25 wherein the step (e) further comprises subtracting the measured $CO_{room}$ from the measured CO and dividing the difference by the determined duty cycle.

27. The method of claim 25 wherein step (a) further comprises passing a stream of room air through a carbon monoxide detector during a second time period and measuring the $CO_{room}$ corresponding to the room carbon monoxide concentration.

28. The method of claim 27 wherein step (a) further comprises measuring an average of the CO concentration in ambient room air over a second period of time.

29. The method of claim 28 further comprising measuring the CO as an average of a first number of discrete average samples obtained at the end of the first time period.

30. The method of claim 25 wherein step (d) further comprises determining the duty cycle based on the sampled breath during the first time period.

31. The method of claim 30 wherein step (d) further comprises:
   (i) detecting the end-tidal portion of a second gas in the sampled breath other than the first gas; and
   (ii) determining the duty cycle as the ratio of the end-tidal portion to the sampled breath portion of the second gas during the first time period.

32. The method of claim 31 wherein the second gas is carbon dioxide.

33. The method of claim 32 wherein step (e) further comprises subtracting the measured $CO_{room}$ from the measured CO and dividing the difference by the determined duty cycle.

34. The method of claim 33 wherein step (a) further comprises passing a stream of room air through a carbon monoxide detector during a second time period and measuring the $CO_{room}$ corresponding to the room carbon monoxide level.

35. The method of claim 34 wherein step (c) further comprises measuring the CO as an average of a first number of discrete average samples obtained at the end of the first time period.

36. The method of claim 32 wherein step (a) further comprises measuring an average carbon monoxide concentration in ambient room air over a second period of time.

37. The method of claim 32 wherein step (d)(ii) further comprises periodically sampling the sensed concentration of carbon dioxide at a first rate during the first time period, wherein step (c) further comprises periodically sampling the sensed concentration of carbon monoxide at a second rate during the first time period.

38. The method of claim 37 wherein the first rate is on the order of 30 Hz and the second rate is on the order of 1.0 Hz.

39. The method of claim 37 wherein the number of average samples is on the order of 5.

40. The method of claim 37 wherein step (c) further comprises low pass filtering the samples of carbon monoxide sensed during the first time period.

41. The method of claim 25 further comprising controlling a device having a first gas analyzer for performing step (a) prior to performing step (b), and providing a first delay period between the performance of steps (a) and (b).

42. The method of claim 41 further comprising providing a second delay period following step (b) each time it is performed and before step (a) is next performed.

43. The method of claim 42 wherein the second delay is on the order of from 1 to 3 minutes.

44. The method of claim 42 wherein the first delay period is on the order of from 1 to 3 minutes.

45. Apparatus for determining the carbon monoxide concentration in the end tidal portion of the exhaled breath flow of a patient, comprising:
   a carbon monoxide gas analyzer having a gas input for receiving a gas sample and a signal output CO representative of the measured concentration of carbon monoxide in the gas sample, said carbon monoxide gas analyzer having a response time that is not sufficiently fast to distinguish the carbon monoxide concentration of the end tidal portion from other portions of a gas sample that is a patient breath flow;
   a carbon dioxide gas analyzer having an input for receiving a gas sample and a signal output CO2 representative of the measured concentration of carbon dioxide in the gas sample, said carbon dioxide gas analyzer having a response time that is sufficiently fast to distinguish the carbon dioxide concentration of the end tidal portion form other portions of a gas sample that is a patient breath flow;
   means for analyzing the signal output CO2 over a given time period and determining a duty cycle for said signal output relative to a preselected signal parameter;
   first means for providing a room air gas sample flow to the carbon monoxide gas analyzer for a first duration so that the carbon monoxide gas analyzer signal output CO corresponds to a background carbon monoxide concentration;
   second means for providing a patient breath flow gas sample flow of a second duration to the carbon monoxide gas analyzer and to the carbon dioxide gas analyzer, wherein the carbon monoxide gas analyzer signal output CO corresponds to an average carbon monoxide concentration near the end of the second duration, the preselected signal parameter corresponds to the patient's end tidal carbon dioxide concentration, and the analyzing means determines the duty cycle of the end tidal portion of the breath flow sample; and
   calculating means for receiving the background carbon monoxide concentration, the average carbon monoxide concentration and the determined duty cycle and calculating therefrom the end tidal carbon monoxide concentration.

46. The apparatus of claim 45 wherein the analyzing means further comprises a first means for comparing the signal output CO2 to a first threshold and determining the duty cycle of the relative portion of said signal CO2 above the threshold for the given time period.

47. The apparatus of claim 45 wherein the first and second providing means further comprise:
   a flow path connecting the gas inputs of the carbon monoxide and carbon dioxide gas analyzers, the flow path having a gas inlet for receiving a gas sample;
   a pump connected to the flow path;
   a switch for operating the pump to cause the gas sample at the gas inlet to flow along the flow path to the carbon monoxide and carbon dioxide gas analyzers.

48. The apparatus of claim 47 further comprising a flow regulator interposed in the flow path for regulating the flow of the gas sample.

49. The apparatus of claim 47 wherein the first and second providing means further comprise:
   a display means for displaying information;
   a first means for indicating on the display means that the flow path inlet is to be placed to sample room air and first means for actuating the switch to pass a sample of room air to the carbon monoxide gas analyzer for a first time period; and
   a second means for indicating that the flow path inlet is to be placed to sample patient breath and second means for actuating the switch to pass a sample of patient breath to the carbon monoxide and carbon dioxide gas analyzers for a second time period, wherein the calculating means calculates the end tidal carbon monoxide concentration following the end of the second time period.

50. The apparatus of claim 45 wherein the calculating means calculates the end tidal carbon monoxide concentration as equal to the quantity of the average carbon monoxide concentration minus the background carbon monoxide concentration divided by the duty cycle, wherein the duty cycle corresponds to the end tidal portion of the patient breath flow gas sample.

* * * * *

UNITED STATES PATENT AND TRADEMARK OFFICE
CERTIFICATE OF CORRECTION

PATENT NO : 5,293,875
DATED : March 15, 1994
INVENTOR(S): Robert T. Stone

It is certified that error appears in the above-indentified patent and that said Letters Patent is hereby corrected as shown below:

Column 9, line 24, delete "respective" and insert --respectively--;

Column 11, line 55, delete "CO" and insert --$CO_2$--;

Column 18, line 55, delete "clam" and insert --claim--;

Column 19, line 36, after "comprising" insert --:--;

Column 20, line 13, after "coupling" insert --to--;

Column 20, line 26, delete "the" and insert --a--;

Column 20, line 34, after "wherein" delete "the"

Signed and Sealed this

Second Day of September, 1997

Attest:

BRUCE LEHMAN

*Attesting Officer*     Commissioner of Patents and Trademarks